(12) United States Patent
McKeon et al.

(10) Patent No.: US 6,620,986 B1
(45) Date of Patent: Sep. 16, 2003

(54) **TRANSFORMATION OF *RICINUS COMMUNIS*, THE CASTOR PLANT**

(75) Inventors: Thomas A. McKeon, Richmond, CA (US); Grace Q. Chen, El Sobrante, CA (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/715,677

(22) Filed: Nov. 16, 2000

Related U.S. Application Data
(60) Provisional application No. 60/167,360, filed on Nov. 23, 1999.

(51) Int. Cl.⁷ ............................................. C12N 15/82
(52) U.S. Cl. ...................................................... 800/294
(58) Field of Search ............................... 800/298, 313, 800/278, 292, 294, 293; 435/468, 469, 470, 419, 430, 430.1

(56) References Cited

U.S. PATENT DOCUMENTS

| | | | |
|---|---|---|---|
| 5,580,768 A | 12/1996 | Boffey et al. | |
| 5,948,682 A | 9/1999 | Moloney | |
| 5,955,646 A | 9/1999 | Gelvin et al. | |
| 6,051,755 A | * 4/2000 | Zou et al. | 800/281 |
| 6,323,395 B1 | * 11/2001 | Rubin-Wilson et al. | 800/281 |

FOREIGN PATENT DOCUMENTS

EP   223417 A1   10/1986

OTHER PUBLICATIONS

Hansen et al., Resent advances in the transformation of plants, Jun. 1999, Trends in plant science, vol. 4, No. 6, pp. 226–231.*

Pradel, K.S. et al., "Structure and function of vascular tissues and histochemical localisation of GUS expression in *Agrobacterium tumefaciens*–induced plant tumors," *Journal od Experimental Botnay* (1996) 47 (Spec Issue):1303.

Pradel K.S. et al., "Evidence for Symplastic Phloem Unloading with Concomitant High Activity of Acid Cell Wall Intertase in *Agrobacterium tumefaciens*–Induced Plant Tumors," *Bot. Acte* (1996) 109:397–404.

Bechtold, N. et al., "In planta Agrobacterium mediated gene transfer by infiltration of adult *Arabidopsis thaliana* plants," *C.R. Acad. Sci. Paris, Sciences de la vie/Life Sciences* (1993) 316:1194–1199.

Clough, S. et al., "Floral dip: a simplified method for Agrobacterium–mediated transformation of *Arabidopsis thaliana*," *The Plant Journal* (1998) 16(6):735–743.

Jefferson, R., "Assaying Chimeric Genes in Plants: The GUS Gene Fusion System," *Plant Molecular Biology Reporter* (1987) 5:387–405.

Molina, S.M. et al., "Micropropagation of *Richinus communis*," *J. Plant Physiol.* (1995) 147:270–272.

Narasimhulu, S.B. et al., "Early Transcription of Agrobacterium T–DNA Genes in Tobacco and Maize," *The Plant Cell* (1996) 8:873–886.

Ni, M. et al., "Strength and tissue specificity of chimeric promoters derived from the octopine and mannopine synthase genes," *The Plant Journal* (1995) 7(4):661–676.

Ooms, G. et al., "Studies on the structure of cointegrates between octopine and nopaline Ti–plasmids and their tumor–inducing properties,"*Plant Molecular Biology* (1982) 1:265–276.

Sujatha, M. et al., "Differential cytokinin effects on the stimulation of in vitro shoot proliferation from meristematic explants of castor (*Ricinus communis* L.)," *Plant Cell Reports* (1998) 17:561–566.

Vancanneyt, G. et al., "Construction of an intron–containing marker gene: Splicing of the intron in transgenic plants and its use in monitoring early events in Agrobacterium–mediated plant transformation," *Mol. Gen. Genet.* (1990) 220:245–250.

Varier, A. et al., "Characterisation of castor (*Ricinus communis* L.) hybrids and inbreds by seed morphology and electrohoresis of seed proteins and isoenzymes," *Seed Sci. & Technol.* (1999) 27:11–21.

* cited by examiner

Primary Examiner—Amy J. Nelson
Assistant Examiner—Anne Kubelik
(74) Attorney, Agent, or Firm—Margaret A. Connor; John Fado (57) ABSTRACT

The invention is a method of Agrobacterium-mediated transformation of castor. The flower bud of an intact castor plant is wounded and Agrobacterium comprises the transgene is infiltrated into the wound. The flower bud is allowed to get seed, and seed comprising the transgene is grown into a transformed castor plant.

1 Claim, 4 Drawing Sheets

FIG. 4

TRANSFORMATION OF *RICINUS COMMUNIS*, THE CASTOR PLANT

CROSS-REFERENCE TO RELATED APPLICATIONS

This application claims the benefit of U.S. Provisional Application No. 60/167,360 filed Nov. 23, 1999. The disclosure of said provisional application is incorporated herein by reference in its entirety.

BACKGROUND OF THE INVENTION

1. Field of the Invention

The present invention relates generally to methods for genetically altering plant materials and reproducing plants therefrom. More particularly, the invention relates to genetic transformation of castor.

2. Description of the Art

Castor (*Ricinus communis* L.) is an important crop of the family Euphorbiaceae. It is a monotypic species of the genus Ricinus and has considerable economic value because of its oil-rich seeds, which yield castor oil, a strategically important oil with numerous industrial uses. The castor bean contains up to 60% oil of unique composition. Chemically, castor is a triglyceride (ester) of fatty acids. Up to 90% of the fatty acid content of the oil is ricinoleic acid (12-hydroxyoleic acid), an 18-carbon acid having a double bond in the 9–10 position and a hydroxyl group on the 12th carbon. As a result, castor oil and products derived from it are used for numerous industrial products, including bio-based lubricants, paints and coatings, plastics, anti-fungal compounds, and cosmetics. The world market for castor oil is 900 million pounds per year. The United States imports 110 million pounds of castor oil per year. One problem in recent years has been the instability in the supply of castor oil. The major suppliers, India and Brazil, have experienced production problems in recent years.

Although there is demand for a dependable supply of castor in the United States, the castor plant is not cultivated in the U.S. because the castor bean from which the oil is obtained also contains the potent toxin ricin and highly allergenic proteins. While breeding of lower toxin strains has been reported, the toxin and allergenic content of castor remain a problem, and workers who handle castor or castor meal can exhibit severe immune reactions, including debilitating hives and asthma. Modification of castor to lessen the hazardous components and make the castor plant suitable for handling by growers and processors is needed to facilitate re-introduction into the United States and acceptance of this important industrial crop which has both an appreciable domestic market and considerable export potential.

Improvement of castor has been limited to traits available in germplasm; however, castor germplasm is of limited use in reducing toxin and allergen content. What is needed is an ability to genetically transform castor and thereby provide a fundamental means to eliminate the hazardous components from the castor and improve agronomic and other traits of castor plants. However, castor has proven recalcitrant to generation of stably transformed plants (S. M. Molina et al., *Plant Physiology* 147: 270–272, 1995; M. Sujatha et al., *Plant Cell Reports* 17: 561–566, 1998), and no such transformation method has been available.

SUMMARY OF THE INVENTION

The invention is directed to castor plants and their seeds, transformed with a transgene, capable of expression in the cells of the castor plant.

The ability to genetically transform the castor plant provides the means to develop castor having new traits. Introduction and expression of a transgene in castor can be used to eliminate hazardous components from the castor plant. For example, expression of genes for allergenic and/or toxic components could be blocked by anti-sense RNA inhibition of gene expression or by co-suppression, thereby making it an acceptable crop to grow domestically by reducing the hazards associated with growing and processing castor beans. This ability will facilitate domestic introduction and acceptance of this important industrial crop.

Additionally, due to its unique biochemistry, castor can be engineered to produce novel oils such as fatty acids with other polar functionalities, for example, epoxy fatty acids. The estimated demand for an epoxy oil is 300 million pounds per year.

In accordance with this discovery, it is an object of the invention to provide methods for genetic transformation of castor, for which there is no precedent, to thereby create castor plants and lines having new traits.

Other objects and advantages of the invention will become readily apparent from the ensuing description.

BRIEF DESCRIPTION OF THE DRAWINGS

FIG. 1 shows GUS expression in leaves of vacuum infiltrated intact castor plants two weeks after transformation. Leaf discs A, B, C, and D are samples from the second set of normal leaves of plant 2, 3, 4, and 7 (Table 1), respectively. GUS staining was performed as described by Jefferson, *Plant Mol. Biol. Rep.* 5:387–405, 1987.

FIG. 2 shows GUS expression in 15-day-old shoot tip cultures. Shoot tips were cultured on MS medium (Murashige and Skoog, 1962) containing 2 mg/l N6-benzyladenine. Transformation was performed in the third day of culture initiation by drop infiltration, followed by co-cultivation of shoot tips with the Agrobacterium for 3 days. GUS staining was performed as described by Jefferson, supra.

FIG. 3 shows GUS expression in 15-day-old embryo axis cultures. Embryo axes were cultured on MS medium containing 5 mg/l thiadiazuron. Transformation was performed in the third day of culture initiation by drop infiltration, followed by co-cultivation of the embryo axes with the Agrobacterium for 3 days. GUS staining was performed as described by Jefferson, supra.

FIG. 4 shows GUS expression in immature seeds from a green fruit about 20 mm in diameter. The stained seeds were transformed with the GUS reporter gene. The unstained (white) seeds are control seeds.

DETAILED DESCRIPTION OF THE INVENTION

The following references provide one of skill with a general definition of many of the terms used in this invention: Singleton, et al., *Dictionary of Microbiology and Molecular Biology* (2d ed. 1994); *The Cambridge Dictionary of Science and Technology* (Walker ed., 1988); *The Glossary of Genetics*, 5th Ed., Rieger, R., et al.(eds.), Springer Verlag (1991); and Hale & Marham, *The Harper Collins Dictionary of Biology* (1991); Sambrook et al., *Molecular Cloning, A Laboratory Manual*, $2^{nd}$ Ed., Cold Spring Harbor Laboratory Press, 1989. All patents and references are herein incorporated by reference in their entirety.

DEFINITIONS

To facilitate understanding of the invention, a number of terms are defined below.

The term "plant" as used herein refers to a plurality of plant cells which are largely differentiated into a structure that is present at any stage of a plant's development. Such structures include, but are not limited to, a fruit, bean, shoot, floral bud, stem, leaf, flower petal, seed, etc. The term "plant tissue" includes differentiated and undifferentiated tissues of plants including, but not limited to, roots, shoots, leaves, pollen, seeds, tumor tissue and various types of cells in culture, including, for example, single cells, protoplasts, embryos, callus). Plant tissue may be in planta, in organ culture, tissue culture, or cell culture.

The term "cell" can refer to any cell from a plant, including but not limited to, somatic cells, gametes or embryos. "Embryo" refers to a sporophytic plant before the start of germination. Embryos can be formed by fertilization of gametes by sexual crossing or by selfing. A "sexual cross" is pollination of one plant by another. "Selfing" is the production of seed by self-pollinization, i.e., pollen and ovule are from the same plant. The term "backcrossing" refers to crossing an $F_1$ hybrid plant to one of its parents. Typically, backcrossing is used to transfer genes which confer a simply inherited, highly heritable trait into an inbred line. The inbred line is termed the recurrent parent. The source of the desired trait is the donor parent. After the donor and the recurrent parents have been sexually crossed, $F_1$ hybrid plants which possess the desired trait of the donor parent are selected and repeatedly crossed (i.e., backcrossed) to the recurrent parent or inbred line.

The term "transgenic" when used in reference to a cell refers to a cell which contains a transgene, or whose genome has been altered by the introduction of a transgene. The term "transgenic" when used in reference to a tissue or to a plant refers to a tissue or plant, respectively, which comprises one or more cells that contain a transgene, or whose genome has been altered by the introduction of a transgene. Transgenic cells, tissues and plants may be produced by several methods including the introduction of a "transgene" comprising nucleic acid (usually DNA) into a target cell or integration of the transgene into a chromosome of a target cell by way of human intervention, such as by the methods described herein.

The term "transgene" as used herein refers to any nucleic acid sequence which is introduced into the genome of a cell by experimental manipulations. A transgene may be a "native DNA sequence," or a "heterologous DNA sequence" (i.e., "foreign DNA"). The term "native DNA sequence" refers to a nucleotide sequence which is naturally found in the cell into which it is introduced so long as it does not contain some modification (e.g. a point mutation, the presence of a selectable marker gene, etc.) relative to the naturally-occurring sequence.

The term "heterologdus DNA sequence" refers to a nucleotide sequence which is ligated to, or is manipulated to become ligated to, a nucleic acid sequence to which it is not ligated in nature, or to which it is ligated at a different location in nature. Heterologous DNA is not endogenous to the cell into which it is introduced, but has been obtained from another cell. Heterologous DNA also includes a native DNA sequence which contains some modification. Generally, although not necessarily, heterologous DNA encodes RNA and proteins that are not normally produced by the cell into which it is expressed. Examples of heterologous DNA include reporter genes, transcriptional and translational regulatory sequences, selectable marker proteins (e.g., proteins which confer drug resistance), etc.

The term "transformation" refers to the introduction of a transgene into a plant cell, either in culture or into the tissues of a plant by a variety of techniques used by molecular biologists. A number of techniques are known in the art for transformation of plants or plant cells in general, including Agrobacterium-mediated transformation, electroporation, microinjection, microprojectile or particle gun technology (biolistics), liposomes, polyethylene glycol (PEG) mediated transformation, wounding, vacuum infiltration, passive infiltration or pressurized infiltration, and reagents that increase free DNA uptake. Identification of transformed cells or plants is generally accomplished by including a selectable marker in the-transforming vector.

For transformation of plants, DNA constructs may be combined with suitable T-DNA flanking regions and introduced into a conventional *Agrobacterium tumefaciens* host vector. The virulence functions of the *Agrobacterium tumefaciens* host will direct the insertion of a transgene and adjacent marker gene(s) (if present) into the plant cell DNA when the cell is infected by the bacteria. *Agrobacterium tumefaciens*-mediated transformation techniques are well described in the scientific literature. See, for example Horsch, et al., *Science* 233:496–498 (1984), Fraley, et al., *Proc. Natl. Acad. Sci. USA* 80:4803 (1983), Hooykaas, *Plant Mol. Biol.*, 13:327–336, Bechtold el al., *Comptes Rendus De L Academie Des Sciences Serie III-Sciences De La Vie-Life Sciences*, 316:1194–1199 (1993), Valvekens et al., *Proc. Natl. Acad Sci. USA*, 85:5536–5540 (1988), and U.S. Pat. Nos. 4,940,838, 5,569,834; 5,416,011; 5,981,839, and 5,981,840, the entire contents of which are herein incorporated by reference.

The term "Agrobacterium" refers to a soil-borne, Gram-negative, rod-shaped phytopathogenic bacterium which causes crown gall. The term "Agrobacterium" includes, but is not limited to, the strains *Agrobacterium tumefaciens*, (which typically causes crown gall in infected plants), and *Agrobacterium rhizogenes* (which causes hairy root disease in infected host plants). Infection of a plant cell with Agrobacterium generally results in the production of opines (e.g., nopaline, agropine, octopine etc.) by the infected cell. Thus, Agrobacterium strains which cause production of nopaline (e.g. strain LBA4301, C58, A208) are referred to as "nopaline-type" Agrobacteria; Agrobacterium strains which cause production of octopine (e.g. strain LBA4404, Ach5, B6) are referred to as "octopine-type" Agrobacteria; and Agrobacterium strains which cause production of agropine (e.g., strain EHA105, EHA101, A281) are referred to as "agropine-type" Agrobacteria.

For transformation mediated by bacterial infection, a plant cell is infected with *Agrobacterium tumefaciens* or *A. rhizogenes* previously transformed with the DNA to be introduced. Agrobacterium is a representative genus of the gram-negative family Rhizobiaceae. Heterologous genetic sequences can be introduced into appropriate plant cells, by means of the Ti plasmid of *A. tumefaciens* or the Ri plasmid of *A. rhizogenes*. The Ti or Ri plasmid is transmitted to plant cells on infection by Agrobacterium and is stably integrated into the plant genome (J. Schell, *Science* 237: 1176–1183 (1987)). Ti and Ri plasmids contain two regions essential for the production of transformed cells.

Construction of recombinant Ti and Ri plasmids in general follows methods typically used with the more common bacterial vectors, such as pUC 19. There are two classes of recombinant Ti and Ri plasmid vector systems now in use.

In one class, called "cointegrate," the shuttle vector containing the gene of interest is inserted by genetic recombination into a non-oncogenic Ti plasmid that contains both the cis-acting and trans-acting elements required for plant transformation as, for example, in the pMLJ1 shuttle vector of DeBlock et al., *EMBO J* 3: 1681–1689 (1984) and the non-oncogenic Ti plasmid pGV3850 described by Zambryski et al., *EMBO J*2: 2143–2150 (1983). In the second class or "binary" system, the gene of interest is inserted into a shuttle vector containing the cis-acting elements required for plant transformation. The other necessary functions are provided in trans by the non-oncogenic Ti plasmid as exemplified by the pBIN19 shuttle vector described by Bevan, *Nucleic Acids Research* 12: 8711–8721 (1984) and the non-oncogenic Ti plasmid PAL4404 described by Hoekema et al., *Nature* 303: 179–180 (1983). Some of these vectors are commercially available. *Agrobacterium tumefaciens*-mediated transformation techniques, including disarming and use of binary vectors, are also well described in the scientific literature. See, for example Horsch, et al., *Science* 233:496–498 (1984), Fraley, et al., *Proc. Nat'l. Acad Sci. USA* 80:4803 (1983), and U.S. Pat. No. 4,940,838, the entire contents of which are herein incorporated by reference.

Vacuum infiltration has been applied to transformation of Arabidopsis with Agrobacterium (N. Bechtold et al., *C. R. Acad Sci. Paris, Life Sciences* 316: 1194–1199, 1993; S. J. Clough et al., *The Plant Journal* 16:735–743, 1998). This method, which involves the adult plant, can be used to eliminate tissue culture and regeneration steps minimizing somaclonal variation which is usually associated with tissue culture. The use of vacuum infiltration for transformation of plant species other than Arabidopsis has not been reported.

Passive or drop infiltration involves dropping the infiltration solution onto the surface of the tissue to be transformed (Clough et al., supra).

The term "wounding" when made in reference to plant tissue refers to the introduction of wounds in that tissue. Wounding of plant tissue may be achieved, for example, by punching, maceration, sonication (see U.S. Pat. No. 5,693, 512), using surfactant or enzymes, or bombardment with microprojectiles, etc. [see, e.g., Bidney et al. (1992) *Plant Molec. Biol.* 18:301–313].

Nucleic acids can be introduced directly into the genomic DNA of the plant cells using techniques such as electroporation and microinjection of plant cell protoplasts, or the DNA constructs can be introduced directly to plant cells using biolistic methods, such as DNA particle bombardment. Particle-mediated transformation techniques (also known as "biolistics" or "biolistic bombardment") refer to the process of accelerating particles towards a target biological sample (e.g., cell, tissue, etc.) to effect wounding of the cell membrane of a cell in the target biological sample and/or entry of the particles into the target biological sample. Methods for biolistic bombardment are known in the art (e.g., U.S. Pat. Nos. 5,015,580 and 5,584,807, the contents of which are herein incorporated by reference), and are commercially available (e.g., the helium gas-driven microprojectile accelerator (PDS-1000/He) (BioRad). Particle bombardment techniques are also described in U.S. Pat. No. 5,914,451; Klein et al., *Nature* 327:70–73, 1987; Vasil et al., *Bio/Technol.*, 11:1553–1558 (1993) and Becker et al., *Plant J*, 5:299–307 (1994). Weeks et al, *Plant Physiol*. 102:1077–1084, 1993, describe the bombardment of calli derived from immature embryos as a preferred method of transforming wheat and other cereals.

Microinjection techniques are known in the art and well described in the scientific and patent literature. The introduction of DNA constructs using polyethylene glycol (PEG) precipitation is described in Paszkowski et al. *EMBO J*. 3:2717–2722 (1984). Polyethylene glycol is described by Krens et al., *Nature* 296:72–74, 1982. Electroporation techniques are described in Fromm et al. *Proc. Natl. Acad Sci. USA* 82:5824 (1985).

Methods by which one can analyze the integration of the introduced exogenous DNA include PCR analysis, antibiotic or herbicide resistance analysis, enzymatic analysis and/or Southern blots to verify transformation. See, e.g., Sambrook et al., *Molecular Cloning—A Laboratory Manual*, Cold Spring Harbor Laboratory, Cold Spring Harbor, N.Y., 1989.

Though some of these methods may have widespread applicability to many plant species, not all plants will respond to a given mode of genetic transformation.

Transformation of a cell may be stable or transient. The term "transient transformation" or "transiently transformed" refers to the introduction of one or more transgenes into a cell in the absence of integration of the transgene into the host cell's genome. Transient transformation may be detected by, for example, enzyme-linked immunosorbent assay (ELISA) which detects the presence of a polypeptide encoded by one or more of the transgenes. Alternatively, transient transformation may be detected by detecting the activity of the protein (e.g. β-glucuronidase) encoded by the transgene (e.g., the uid A gene) [e.g., histochemical assay of GUS enzyme activity by staining with X-gluc which gives a blue precipitate in the presence of the GUS enzyme; and a chemiluminescent assay of GUS enzyme activity using the GUS-Light kit (Tropix)]. The term "transient transformant" refers to a cell which has transiently incorporated one or more transgenes. In contrast, the term "stable transformation" or "stably transformed" refers to the introduction and integration of one or more transgenes into the genome of a cell. Stable transformation of a cell may be detected by Southern blot hybridization of genomic DNA of the cell with nucleic acid sequences which are capable of binding to one or more of the transgenes. Alternatively, stable transformation of a cell may also be detected by enzyme activity of an integrated gene in growing tissue or by the polymerase chain reaction of genomic DNA of the cell to amplify transgene sequences. The term "stable transformant" refers to a cell which has stably integrated one or more transgenes into the genomic or organellar DNA.

The term "nucleotide sequence of interest" refers to any nucleotide sequence, the manipulation of which may be deemed desirable for any reason (e.g., confer improved qualities), by one of ordinary skill in the art. Such nucleotide sequences include, but are not limited to, coding sequences of genes for enzymes or structural proteins (e.g., reporter genes, selection marker genes, ricin toxin genes, pathogens or herbicide resistance genes, lipid biosynthetic genes, fatty acid modification genes, storage protein genes, albumin genes, insecticidal genes, etc.), and non-coding regulatory sequences which do not encode an mRNA or protein product, (e.g., promoter sequence, polyadenylation sequence, termination sequence, enhancer sequence, etc.).

The term "isolated" when used in relation to a nucleic acid, as in "an isolated nucleic acid sequence" refers to a nucleic acid sequence that is present in a form or setting that is different from that in which it is found in nature. In contrast, non-isolated nucleic acids are nucleic acids such as DNA and RNA which are found in the state they exist in nature.

The phrase "hybridizes under stringent conditions" refers to the formation of a double-stranded duplex by two single-stranded nucleic acids. The region of double-strandedness can include the full-length of one or both of the single-stranded nucleic acids, or all of one single stranded nucleic acid and a subsequence of the other single stranded nucleic acid, or the region of double-strandedness can include a subsequence of each nucleic acid. An extensive guide to the hybridization of nucleic acids is found in Tijssen, *Laboratory Techniques in Biochemistry and Molecular Biology—Hybridization with Nucleic Acid Probes* Parts I and II, Elsevier, N.Y., (1993). Generally, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Highly stringent conditions are selected to be equal to the $T_m$ point for a particular probe.

An example of stringent hybridization conditions for hybridization of complementary nucleic acids that have more than 100 complementary residues on a filter in a Southern or northern blot is 50% formalin with 1 mg of heparin at 42° C., with the hybridization being carried out overnight. An example of stringent wash conditions for a Southern blot of such nucleic acids is a 0.2×SSC wash at 65° C. for 15 minutes (see, Sambrook, et al., *Molecular Cloning—A Laboratory Manual* (2nd ed.) Vol. 1–3, Cold Spring Harbor Laboratory, Cold Spring Harbor Press, New York, 1989 (Sambrook) for a description of SSC buffer). Often the high stringency wash is preceded by a low stringency wash to remove background probe signal. An example low stringency wash is 2×SSC at 40° C. for 15 minutes. In general, a signal to noise ratio of 2× (or higher) than that observed for an unrelated probe in the particular hybridization assay indicates detection of a specific hybridization. For highly specific hybridization strategies such as allele-specific hybridization, an allele-specific probe is usually hybridized to a marker nucleic acid (e.g., a genomic nucleic acid, or the like) comprising a polymorphic nucleotide under highly stringent conditions. "Nucleic acid sequence homologs" refers to deoxyribonucleotides or ribonucleotides and polymers thereof in either single- or double-stranded form containing known analogs of natural nucleotides, which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer, et al., *Nucleic Acid Res.* 19:5081 (1991); Ohtsuka, etal., *J. Biol. Chem.* 260:2605–2608 (1985); and Rossolini, et al., *Mol. Cell. Probes* 8:91–98 (1994)).

The phrase "introducing a nucleic acid sequence" refers to introducing nucleic acid sequences by recombinant means, including but not limited to, Agrobacterium-mediated transformation, biolistic methods, electroporation, in planta techniques, and the like. The term "nucleic acids" is synonymous with DNA, RNA, polydeoxyribonucleotides, and polyribonucleotides. Such a plant containing the nucleic acid sequences is referred to here as an $R_1$ or to generation plant. $R_1$ or to plants may also arise from cloning, sexual crossing or selfing of plants into which the nucleic acids have been introduced.

"Transgenic plants" are plants into which the nucleic acid has been introduced through recombinant techniques, e.g., nucleic acid-containing vectors.

A "vector" is a nucleic acid composition which can transduce, transform or infect a cell, thereby causing the cell to express vector-encoded nucleic acids and, optionally, proteins other than those native to the cell, or in a manner not native to the cell. A vector includes a nucleic acid (ordinarily RNA or DNA) to be expressed by the cell. A vector optionally includes materials to aid in achieving entry of the nucleic acid into the cell, such as a retroviral particle, liposome, protein coating or the like. Vectors contain nucleic acid sequences which allow their propagation and selection in bacteria or other non-plant organisms. For a description of vectors and molecular biology techniques, see *Current Protocols in Molecular Biology*, Ausubel, et al., (eds.), Current Protocols, a joint venture between Greene Publishing Associates, Inc. and John Wiley & Sons, Inc., (through and including the 1998 Supplement) (Ausubel).

The phrase "expression cassette" refers to a nucleic acid sequence within a vector which is to be transcribed, and a promoter to direct the transcription. The term "promoter," "promoter element," or "promoter sequence" as used herein, refers to a DNA sequence which when ligated to a nucleotide sequence of interest is capable of controlling the transcription of the nucleotide sequence of interest into mRNA. A promoter is typically, though not necessarily, located 5' (i.e., upstream) of a nucleotide sequence of interest whose transcription into mRNA it controls, and provides a site for specific binding by RNA polymerase and other transcription factors for initiation of transcription. A promoter also optionally includes distal enhancer or repressor elements which can be located as much as several thousand base pairs from the start site of transcription or from the stop site. The promoter can either be homologous or heterologous.

Promoters may be tissue specific or cell specific. The term "tissue specific" as it applies to a promoter refers to a promoter that is capable of directing selective expression of a nucleotide sequence of interest to a specific type of tissue (e.g., seeds or endosperm) in the relative absence of expression of the same nucleotide sequence of interest in a different type of tissue (e.g., stems). Tissue specificity of a promoter may be evaluated by, for example, operably linking a reporter gene to the promoter sequence to generate a reporter construct, introducing the reporter construct into the genome of a plant such that the reporter construct is integrated into every tissue of the resulting transgenic plant, and detecting the expression of the reporter gene (e.g., detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected.

The term "cell type specific" as applied to a promoter refers to a promoter which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., immunohistochemical staining. Briefly, tissue sections are embedded in paraffin, and paraffin sections are reacted with a primary antibody which is specific for the polypeptide product encoded by the nucleotide sequence of interest whose expression is controlled by the promoter. A labeled (e.g., peroxidase conjugated) secondary antibody which is specific for the primary antibody is allowed to bind to the sectioned tissue and specific binding detected (e.g., with avidin/biotin) by microscopy.

Promoters may be constitutive or regulatable. The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue. In contrast, a "regulatable" promoter is one which is capable of directing a level of transcription of an operably linked nucleic acid sequence in the presence of a stimulus (e.g., heat shock, chemicals, light, etc.) which is different from the level of transcription of the operably linked nucleic acid sequence in the absence of the stimulus.

For example, a constitutive plant promoter fragment may be employed which will direct expression in all tissues oaf plant. Such promoters are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumefaciens*, and other transcription initiation regions from various plant genes known to those of skill.

Alternatively, the plant promoter may be under environmental control, e.g., "inducible" promoters. Examples of environmental conditions that may effect transcription by inducible promoters include pathogen attack, anaerobic conditions, or the presence of light.

Promoters that direct expression in seeds, especially the endosperm are of particular interest. Examples of such promoters include the promoter from genes encoding seed storage proteins, such as napin, cruciferin, phaseolin, and the like (see, U.S. Pat. No. 5,420,034). Other promoters suitable for expressing genes in plants include promoters from genes encoding enzymes that modify fatty acid such as hydroxylases, enzymes involved in lipid biosynthesis such as diacylglycerol acyltransferase or proteins involved in lipid storage, e.g., oleosins.

The phrase "operably encodes" refers to the functional linkage between a promoter and a second nucleic acid sequence, wherein the promoter sequence initiates transcription of RNA corresponding to the second sequence.

The phrase "prevents expression of a protein" refers to inhibition of the synthesis of a specified protein in the cells of a plant. Inhibition can be either at the transcription level, i.e., synthesis of corresponding mRNA, or the translation level, i.e., synthesis of protein. For purposes of this invention, preventing expression of proteins is accomplished through the introduction of nucleic acid sequences which suppress synthesis of mRNA or protein. The nucleic acid may encode mRNA transcripts that inhibit expression of genes. For example, anti-sense RNA inhibition of gene expression has been shown; see, e.g., Sheehy, et al., *Proc. Natl. Acad. Sci. USA* 85:8805–8809 (1988), and U.S. Pat. No. 4,801,340. Catalytic RNA molecules or ribozymes can also be used to inhibit expression of specific genes. The design and use of target RNA-specific ribozymes is described in Haseloff et al. *Nature*, 334:585–591 (1988). Introduction of nucleic acid configured in the sense orientation has also been shown to be an effective means by which to block the transcription of target genes. For an example of the use of sense suppression to modulate expression of endogenous genes, see, Napoli, et al., *The Plant Cell* 2:279–289 (1990), and U.S. Pat. No. 5,034,323.

Antisense technology comprises cloning a nucleic acid segment from the desired gene and operably linking it to a promoter such that the antisense (or complementary) strand of RNA will be transcribed. The construct is then transformed into plants and the antisense strand of RNA is produced.

The nucleic acid segment to be introduced generally will be substantially identical to at least a portion of the gene or genes to be suppressed. The sequence, however, need not be perfectly identical to inhibit expression. The introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about 2000 nucleotides should be used, though a sequence of at least about 100 nucleotides is preferred, a sequence of at least about 200 nucleotides is more preferred, and a sequence of at least about 500 nucleotides is especially preferred.

Once transgenic plant tissue which contains an expression vector has been obtained, transgenic plants are regenerated from this transgenic plant tissue. The term "regeneration" as used herein, means growing a whole plant from a plant cell, a group of plant cells, a plant part or a plant piece. Transformed plant cells which are derived by any of the above transformation techniques are cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the nucleic sequence of interest. Regeneration techniques for regenerating plants from plant callus, explants, organs, or parts thereof are described generally in Klee et al. *Ann. Rev. of Plant Phys.* 38:467–486 (1987). The culture media will generally contain various organic components including vitamins, sugars, and plant hormones, such as auxin and cytokinins, as well as inorganic salts. The regenerated plants are transferred to standard soil conditions and cultivated in a conventional manner.

Confirmation of the transgenic nature of the cells, tissues, and plants may be performed by PCR analysis, antibiotic or herbicide resistance, enzymatic analysis and/or Southern blots to verify transformation. Progeny of the regenerated plants may be obtained and analyzed to verify whether the transgenes are heritable. Heritability of the transgene is further confirmation of the stable transformation of the transgene in the plant. Progeny may be sexually or asexually derived progeny.

After the expression cassette is stably incorporated into regenerated transgenic plants, it can be transferred to other plants by sexual crossing. The plants are then grown and harvested using conventional procedures.

TRANSFORMATION OF *RICINUS COMMUNIS* THE CASTOR PLANT

The invention is directed to castor plants, transformed with a transgene capable of being expressed in the castor plant.

As discussed above, castor has been intransigent to transformation, and prior attempts to obtain genetic transformants of castor have failed. We have ascertained that Agrobacterium-mediated drop infiltration and vacuum infiltration of castor plants and selected tissues of castor, can be successfully used to introduce transgenes into, the plant. There are also indications that explants of castor respond favorably to biolistic transformation.

Generating Transgenic Plants

A. Preparation of the Vector. The present invention provides methods for expressing a nucleotide sequence of interest in a cell, tissue, organ, and/or organism. In one embodiment, this is accomplished by introducing into a plant cell a vector that contains a nucleotide sequence of interest operably linked to sequences which have promoter activity. The transformed plant cell is allowed to develop into a transgenic plant in which the nucleotide sequence of interest is expressed.

The invention is not limited to vectors which express a single nucleic acid sequence of interest. Vectors which contain a plurality of (i.e., two or more) nucleic acid sequences under the transcriptional control of the same promoter sequence are expressly contemplated to be within the scope of the invention. Such vectors may be desirable, for example, where the expression products of the plurality of nucleic acid sequences contained within the vector are desired. Also included within the scope of this invention are vectors which contain the same or different nucleic acid sequences under the transcriptional control of different promoter sequences.

B. Nucleotide sequence introduced. The nucleotide sequence is any sequence, the manipulation of which is deemed desirable for any reason (e.g., confer improved qualities). Such nucleotide sequences include, but are not limited to, coding sequences of genes for enzymes or structural proteins (e.g., reporter genes, selection marker genes, ricin toxin genes, pathogens or herbicide resistance genes, lipid biosynthetic genes, fatty acid modification genes, storage protein genes, albumin genes, insecticidal genes, etc.), and non-coding regulatory sequences which do not encode an mRNA or protein product, (e.g., promoter sequence, polyadenylation sequence, termination sequence, enhancer sequence, etc.).

i. Reporter genes. Exemplary reporter genes include but are not limited to genes for beta-glucuronidase, intron and intron-less types, and green fluorescent protein.

ii. Selectable marker genes. Exemplary selectable marker genes include but are not limited to genes for kanamycin resistance, Basta resistance, hygromycin resistance, glyphosate resistance and other herbicide resistance.

iii. Other nucleotide sequences of interest. Other exemplary nucleotide sequences of interest include but are not limited to the following: the endogenous gene for 2S albumin, the source of potent castor allergen, for use in the sense direction or complementary direction for suppression, or altered nucleotide sequence to alter protein sequence in order to eliminate allergenicity. Exemplary nucleotide sequences for horticultural improvements include sequences for *Bacillus thuringiensis* (*B.t.*) toxin and herbicide tolerance. Examples of particularly suitable DNA sequences encoding B.t. toxin protein are described in the EP patent application 385,962 entitled "Synthetic Plant Genes and Method for Preparation," published Sep. 5, 1990.

To reduce toxicity, castor is engineered with the ricin toxin gene so as to reduce the toxin level in the crop. Ricin toxins are described by Horn et al. in U.S. Pat. No. 5,538,868, Piatak, Jr. in U.S. Pat. No. 5,840, 522, and Lord et al. U.S. Pat. No. 5,622,838.

Useful genes to alter the fatty acid composition of the castor oil to change its uses for industrial and other chemical purposes include genes for fatty acyl-epoxidase or fatty acyl-desaturase as well as the endogenous gene for fatty acyl-hydroxylase. Examples of such fatty acid modifying genes are described by Sommerville et al. in U.S. Pat. No. 5,801,026, by Hitz in U.S. Pat. No. 5,846,784, and by Hildebrand et al. in U.S. Pat. No. 5,866,789. Genes that alter fatty acid deposition in oils, for example, the plant lysophosphatidic acid acyltransferases described by Davies et al. in U.S. Pat. No. 5,824,858, are useful to enhance the content of specific-fatty acids. Such genetic changes improve the growing, production and processing potential of the castor plant and enhance the marketability of the resultant castor bean derived oil.

C. Promoters. Promoters include but are not limited to those that are constitutive, allowing the gene to be expressed throughout the plant, and seed-specific, limiting the gene to expression in the seed during a specific developmental interval determined by the genetic properties of the promoter. Exemplary constitutive promoters include the 35S CaMV, the double 35SCaMV, and the (ocs)3mas. Exemplary seed-specific promoters include the napin promoter, exogenous oleosin, endogenous oleosin and the phytohemagglutinin promoter. U.S. Pat. No. 5,955,646 describes promoters plus activating sequences for expression of genes in plants.

Plants/Explant Material

Plant material for transformation includes intact plants or explant tissue such as shoot tips, embryo, stem, leaf disk, floral buds, hypocotyl, and cotyledon. When the intact plant is the plant material source, the preferred transformation tissue is shoot tip, and floral buds. The preferred explant transformation tissue is shoot tip and embryo.

Introduction of Nucleic Acid

Once an expression vector is prepared, transgenic plants and plant cells are obtained by introducing the expression vector into plants and plant cells using methods known in the art. Transformation methods include Agrobacterium-mediated transformation, electroporation, ultrasound, microinjection, microprojectile or particle gun technology, liposomes, and chemicals that increase free DNA uptake. Agrobacterium-mediated transformation methods include wounding, vacuum infiltration, passive (drop) infiltration or pressurized infiltration or combinations thereof.

Agrobacterium-mediated transformation using vacuum infiltration, drop infiltration, or combination of wounding and infiltration on intact plants and explants is described in detail, below, in Examples 1–3. Biolistic transformation is described in Example 4.

Culture Conditions

Typical conditions are described in the Examples, below. For tissue culture typical conditions are as follows: a basal medium of Murashige and Skoog (MS) salts (Murashige and Skoog, *Physiol. Plant*. 15:473–497, 1962) and B5 vitamins (Gamborg et al., *Exp. Cell. Res*. 50:151–158, 1968) with 3% sucrose and 0.7% agar is used. Seeds (for the shoot tip studies) or decoated seeds (for the embryo axes studies) are surface sterilized with a solution of 5% bleach and 0.1% Tween 20 for 15 minutes followed by five rinses in sterile water. To promote and synchronize the germination, seeds are germinated in a germination medium consisting of half strength MS salts supplemented with 0–100 µM ethephon or 1–10 ppm ethylene, and 0.7% agar. Shoot apices of about 3–10 mm length are excised from the epicotyls of about 7–14-day-old seedlings and placed vertically with the cut end in contact with the medium. Embryos are carefully dissected out from the decoated seeds followed by excision of cotyledons, and the embryo axes are cultured. The shoot tips and the embryo axes are pre-cultured in the basal MS medium supplemented with 1–5 mg/l N6-benzyladenine (BA) and 1–10 mg/l thiadiazuron (TDZ), respectively, for 2–3 days. After Agrobacterium-mediated transformation (3 days), plant tissues are transferred into fresh pre-culture medium, with carbenicillin 500 mg/l to inhibit the overgrowth of Agrobacteria, to further initiate shoot induction for 2–3 weeks. The proliferating shoot clusters are transferred into a subculture medium consisting of basal MS medium supplemented with 0.2–0.5 mg/l BA for multiplication and elongation. Shoots longer than 0.5 cm are subcultured in basal MS medium plus 0.2 mg/l BA and 0.1 mg/l gibberellic acid (GA3) for further elongation of shoots. To select transformants and induce root formation, elongated shoots (>1.0 cm) are cultured in the half-strength basal medium supplemented with 50–100 mg/l kanamycin (Km) and 1.0 mg/l indole-3-butyric acid (IBA). True transformants develop roots after 10 days.

After biolistic transformation, the plant tissues are transferred into fresh pre-culture medium to further initiate shoot induction for 2–3 weeks. The proliferating shoot cultures are transferred into the subculture basal MS medium supplemented with 0.5 mg/l BA for multiplication and elongation. Shoots longer than 0.5 cm are subcultured in basal medium plus 0.2 mg/l BA and 0.1 mg/l gibberellic acid (GA3) for further elongation of shoots. To select transformants and induce root formation, elongated shoots (>1.0 cm) are cultured in the half-strength basal medium supplemented with 50 mg/l kanamycin (Km) and 1.0 mg/l indole-3-butyric acid (IBA). True transformants develop roots after 10 days.

These represent conditions that work optimally for transformation and regeneration of castor after transformation. Other conditions that work include, but are not limited to: cytokinin (such as, but not limited to BA, kinetin) concentration ranging from 0 to 10 mg/l; cytokinin analogue (such as, but not limited to thiadiazuron) concentration ranging from 0 to 50 mg/l; auxin (such as, but not limited to indole-3-butyric acid, 2,4-dichlorophenoxyacetic acid, IAA or NAA) 0 to 10 mg/l; gibberellin (such as, but not limited to GA3) 0 to 10 mg/l.

Selection of Transformed Plant Cells

Plants, plant cells and tissues transformed with a heterologous nucleic acid sequence of interest are readily detected using methods known in the art including, but not limited to, GUS assay, restriction mapping of the genomic DNA, PCR-analysis, DNA-DNA hybridization, DNA-RNA hybridization, DNA sequence analysis and the like.

Additionally, selection of transformed plant cells may be accomplished using a selection marker gene. A selection marker gene may confer positive or negative selection.

A positive selection marker gene may be used in constructs for random integration and site-directed integration. Positive selection marker genes include antibiotic resistance genes, and herbicide resistance genes and the like. In one embodiment, the positive selection marker gene is the NPTII gene which confers resistance to geneticin (G418) or kanamycin. In another embodiment the positive selection marker gene is the HPT gene which confers resistance to hygromycin. The choice of the positive selection marker gene is not critical to the invention as long as it encodes a functional polypeptide product. Positive selection genes known in the art include, but are not limited to, the ALS gene (chlorsulphuron resistance), and the DHFR-gene (methothrexate resistance).

A negative selection marker gene may also be included in the constructs. The use of one or more negative selection marker genes in combination with a positive selection marker gene is preferred in constructs used for homologous recombination. Negative selection marker genes are generally placed outside the regions involved in the homologous recombination event. The negative selection marker gene serves to provide a disadvantage (preferably lethality) to cells that have integrated these genes into their genome in an expressible manner. Cells in which the targeting vectors for homologous recombination are randomly integrated in the genome will be harmed or killed due to the presence of the negative selection marker gene. Where a positive selection marker gene is included in the construct, only those cells having the positive selection marker gene integrated in their genome will survive.

The choice of the negative selection marker gene is not critical to the invention as long as it encodes a functional polypeptide in the transformed plant cell. The negative selection gene may for instance be chosen from the aux-2 gene from the Ti-plasmid of Agrobacterium, the tk-gene from SV40, cytochrome P450 from *Streptomyces griseolus*, the Adh-gene from Maize or Arabidopsis, etc. Any gene encoding an enzyme capable of converting a substance which is otherwise harmless to plant cells into a substance which is harmful to plant cells may be used.

Regeneration

Culture regeneration conditions are describe above. The regenerated plants are transferred to standard soil conditions and cultivated in a conventional manner. Confirmation of the transgenic nature of the cells, tissues, and plants may be performed by GUS assay, PCR analysis, antibiotic or herbicide resistance, enzymatic analysis and/or Southern blots to verify transformation. Progeny of the regenerated plants may be obtained and analyzed to verify whether the transgenes are heritable. Heritability of the transgene is further confirmation of the stable transformation of the transgene in the plant. After the expression cassette is incorporated into regenerated transgenic plants, it can be transferred to other plants by sexual crossing. Any of a number of standard breeding techniques can be used, depending upon the species to be crossed. The plants are then grown and harvested using conventional procedures.

EXAMPLES

The following examples are intended only to further illustrate the invention and are not intended to limit the scope of the invention which is defined by the claims.

Example 1

The following example describes Agrobacterium-mediated transformation of intact castor plants.

Plant Material and Plant Growth Conditions. The castor (*Ricinus communis* L.) Accession, PI 215769, was obtained from the U.S. Department of Agriculture, Agricultural Research Service, Southern Regional Plant Introduction Station, Griffin, Ga. Plants were germinated and grown in Sunshine mix, a commercially available mix, in a greenhouse at about 28° C. (day) and about 18° C. (night), with supplemental metal halide lighting (14 hours). The light level on a sunny day was about 1250 μmol/m²/s.

Bacterial Strain and Plasmid. The *Agrobacterium tumefaciens* strain LBA4404 (Ooms et al, *Plant Mol. Biol.* 1:265–276, 1982; Gibco-BRL Electromax LBA4404 Cells) containing the plasmid pBISN1 (Narasimhulu et al., *The Plant Cell*, 8:873–886, 1996 and Ni et al., *The Plant Journal* 7:661–676, 1995) was used for transformation. In brief, the binary vector pBISN1 contains a constitutive $(ocs)_3mas$ promoter (see U.S. Pat. No. 5,955,646) fused to a GUS-intron gene. This intron-containing GUS gene permits early detection of GUS activity in plant cells without interfering GUS activity from contaminating Agrobacteria cells (Vancanneyt et al., *Mol. Gen. Genet.* 220:245–250, 1990). The plasmid was transferred into the Agrobacterium by regular electroporation (Bio-Rad protocol). Agrobacteria were grown at 28° C., 300 rpm in liquid LB medium (10 g tryptone, 5 g yeast extract, 5 g NaCl per liter water, pH 7.0) with 50 mg/l kanamycin. Cultures were started with 1:100 dilution of smaller overnight culture, and grown for 24 hours.

Transformation. Overnight Agrobacterium cultures with an $OD_{600}$ of 0.8–1.0 were diluted to 1:1 in 2×infiltration solution consisting of 10% sucrose and 0.1% of the commercial organosilicone surfactant Silwet® L-77 (Lehle Seeds). For vacuum infiltration, plants were uprooted and infiltrated when they were about 20–25 cm tall. At this stage, the plants of this castor accession had developed their first set of normal leaves and their second set had emerged. The cotyledons and the first set of normal leaves of the uprooted plants were trimmed away. The plants were inverted into a beaker containing Agrobacterium infiltration solution such that all shoot tips including the second set of normal leaves and the trimmed sites on the stem portion were submerged in the suspension. The beaker was placed into a vacuum desiccator and a vacuum was applied until the solution bubbled. The negative pressure was held for 10 minutes and then released slowly over 1 minute. Vacuum infiltrated plants were then removed from the beaker, repotted and placed in a low light location for one week before returning to the greenhouse. The vacuum infiltration experiments were repeated twice.

Histochemical GUS Detection. GUS expression was detected by staining the leaf discs with 5-bromo-4-chloro-3-indolyl glucuronide (X-Gluc, Rose Scientific) as described by Jefferson, *Plant Mol. Biol. Rep.* 5:387–405, 1987. After 18 hours staining, the chlorophyll in leaf discs was washed away with 70% ethanol, and the blue GUS staining was observed.

Figure 1:
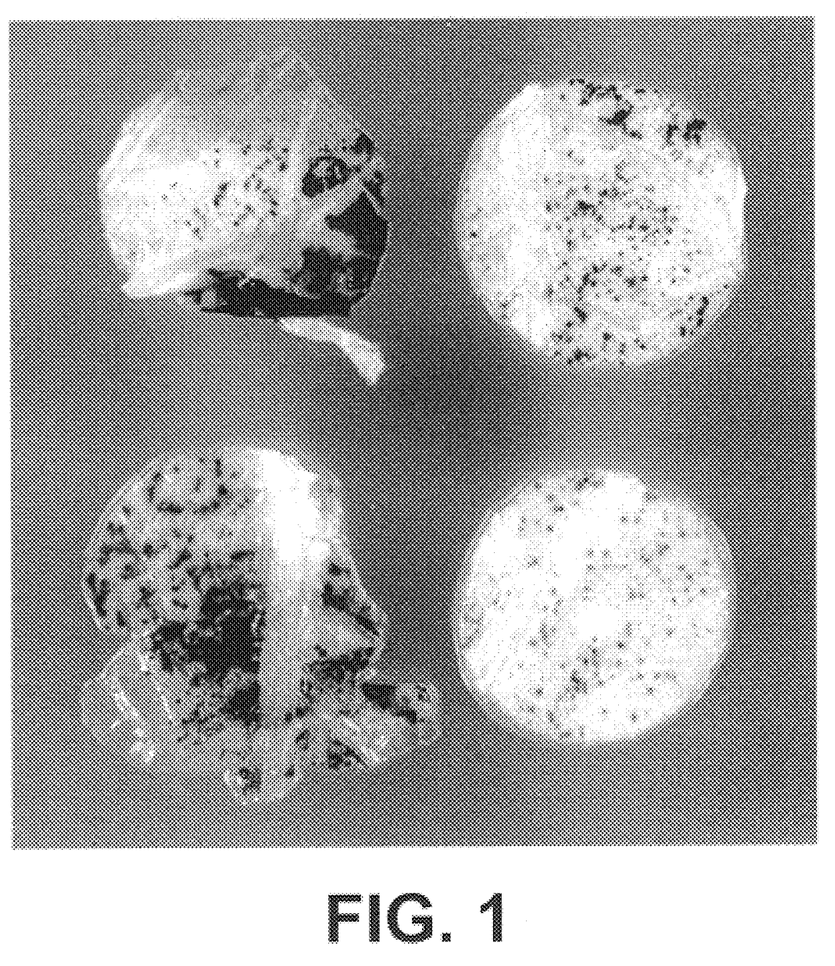

Results. Leaf discs from the second set of normal leaves were taken from vacuum infiltrated plants after the plants were placed in the greenhouse for another week. The results are shown in FIG. 1 and Table 1. As shown in Table 1, the GUS staining was detected in the transformed leaf cells of all 8 plants in the first experiment, and in 6 out of 10 plants in a second experiment. The pattern of GUS staining in each GUS positive leaf disc varied among samples. While some discs had patches of staining, others had dot-like staining. This suggests that either a group of adjacent cells or singles cells were transformed. The mosaic pattern indicates stable transformation of multiple cells.

In sum, the results of our studies demonstrate the Agrobacterium-mediated transformation of intact castor plants.

TABLE 1

GUS expression in the vacuum infiltrated plants

| Plant # | No. of leaf discs tested | No. of GUS positive leaf disc |
|---|---|---|
| Experiment 1 | | |
| 1 | 4 | 1 |
| 2 | 3 | 3 |
| 3 | 5 | 4 |
| 4 | 4 | 4 |
| 5 | 5 | 4 |
| 6 | 10 | 1 |
| 7 | 4 | 4 |
| 8 | 5 | 4 |
| Experiment 2 | | |
| 9 | 2 | 1 |
| 10 | 2 | 1 |
| 11 | 4 | 3 |
| 12 | 4 | 2 |
| 13 | 1 | 4 |
| 14 | 3 | 2 |
| 15 | 3 | 0 |
| 16 | 3 | 0 |
| 17 | 5 | 3 |
| 18 | 2 | 0 |
| 19 | 2 | 0 |

Example 2

The following example describes Agrobacterium-mediated transformation of isolated shoot tips and embryo axes.

Seeds were obtained from castor Accession, PI 215769 described in Example 1. The bacterial strain and plasmid used are as described in Example 1.

Transformation. For shoot tips and embryo axes transformation, the explants were inoculated with Agrobacterium cultures of LBA4404 (Ooms et al., 1982; Gibco-BRL Electromax LBA4404 Cells) containing the plasmid pBISN1 (Ni et al., 1995) by dropping the Agrobacterium infiltration solution (described in Example 1), on to the surface of the explants.

Culture Conditions. For tissue culture, a basal medium of Murashige and Skoog (MS) salts (Murashige and Skoog, *Physiol. Plant.* 15:473–497, 1962) and B5 vitamins (Gamborg et al., *Exp. Cell. Res.* 50:151–158, 1968) with 3% sucrose and 0.7% agar was used. Seeds (for the shoot tip studies) or decoated seeds (for the embryo axes studies) were surface sterilized with a solution of 5% bleach and 0.1% Tween 20 for 15 minutes followed by five rinses in sterile water. To promote and synchronize the germination, seeds were germinated in a germination medium consisting of half strength MS salts supplemented with 10 μM ethephon and 0.7% agar. Shoot apices of 3–5 mm length were excised from the epicotyls of 10-day-old seedlings and placed vertically with the cut end in contact with the medium. Embryos were carefully dissected out from the decoated seeds followed by excision of cotyledons, and the embryo axes were cultured. The shoot tips and the embryo axes were pre-cultured in the basal MS medium supplemented with 2 mg/l N6-benzyladenine (BA) and 5 mg/l thiadiazuron (TDZ), respectively, for 2–3 days. After Agrobacterium-mediated transformation (3 days), plant tissues were transferred into fresh pre-culture medium, with carbenicillin 500 mg/l to inhibit the overgrowth of Agrobacteria, to further initiate shoot induction for 2–3 weeks. The proliferating shoot clusters were transferred into a subculture medium consisting of basal MS medium supplemented with 0.5 mg/l BA for multiplication and elongation. Shoots longer than 0.5 cm were subcultured in basal MS medium plus 0.2 mg/l BA and 0.1 gibberellic acid (GA3) for further elongation of shoots. To select transformants and induce root formation, elongated shoots (>2.0 cm) are cultured in the half-strength basal medium supplemented with 50 mg/l kanamycin (Km) and 1.0 mg/l indole-3-butyric acid (IBA). True transformants develop roots after 10 days.

Histochemical GUS Detection. GUS expression was detected by staining the shoot tips and the embryo axes with 5-bromo-4-chloro-3-indolyl glucuronide (X-Gluc, Rose Scientific) as described by Jefferson, *Plant MoL Biol. Rep.* 5:387–405, 1987. After 18 hours staining, the chlorophyll in the shoot tips and embryo axes cultures was washed away with 70% ethanol, and the blue GUS staining was observed.

Figure 2:
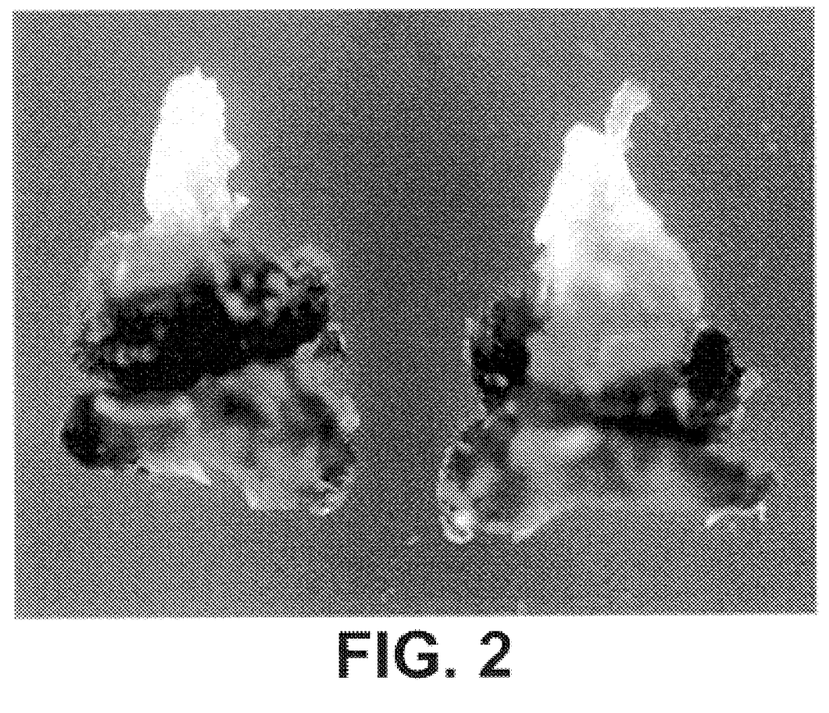
Figure 3:
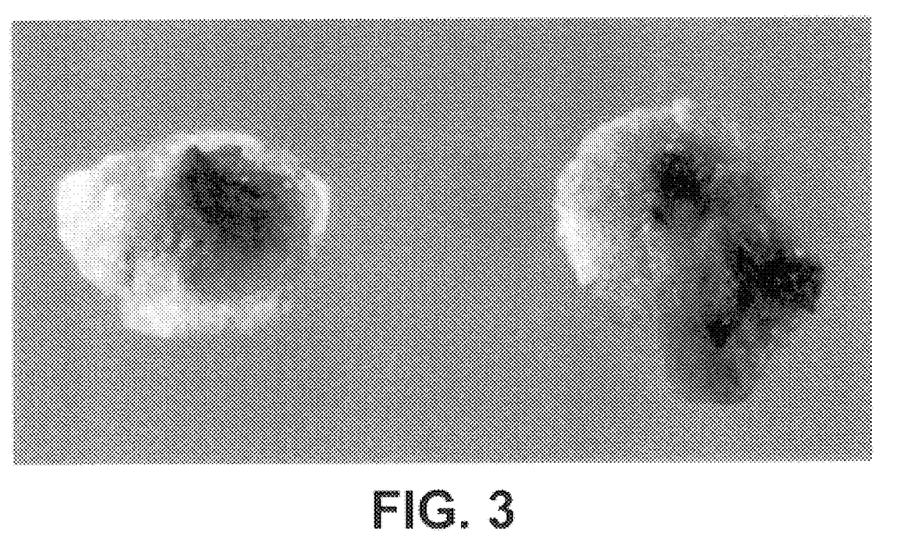

Results. FIGS. 2 and 3 show GUS expression in 15-day-old shoot tip cultures and 15-day-old embryo axis cultures, respectively. As can be seen, the GUS expression was detected with stronger staining in the side of shoot tips (FIG. 2) and in the top of embryo axes (FIG. 3).

Experiments were carried out as described above except that the transformation was preformed by vacuum infiltrating the explants in the Agrobacterin infiltration solution for 10 minutes.

Example 3

The following example describes Agrobacterium-mediated transformation of floral buds of castor plants.

Plant Material and Plant Growth Conditions were described in Example 1. The bacterial strain and plasmid used are as described in Example 1.

Transformation. The Agrobacterium-mediated transformation of mature castor plants was performed when the floral buds were evident. The female flower buds were pre-wounded by scratching on the sides of unopened perianth using a needle (23G size), then inoculated with Agrobacterium by dropping the Agrobacterium infiltration solution on to the surface of immature flowers. The treated flower bud was covered by a 2×3 inch plastic bag to keep moist for 2 days. During the time between the emerging of flower buds and the opening of pistils, the female flower buds were inoculated more than once (see Table 2) but without further wounding and without covering with a plastic bag. The multiple inoculations were stopped when the pistils of female flowers began to open. The flowers were allowed to set seeds.

Transienic Selection. Seeds collected from the treated plants were surface sterilized as described in Example 2. To promote and synchronize the germination, seeds were germinated in a germination medium consisting of half strength MS salts and 0.7% agar in 2ppm ethylene. The germinated seeds were placed in a selection medium that is germination medium supplemented with 50 mg/l kanamycin. Non-transgenic seeds died, while transformants continued to grow.

Immature seeds GUS assay. Immature seeds were dissected out from green fruits when the fruits developed to a size between 5 to 20 mm in diameter. The GUS assay was carried out as described, and the blue GUS staining was observed using a dissecting microscope when it was needed.

Figure 4:
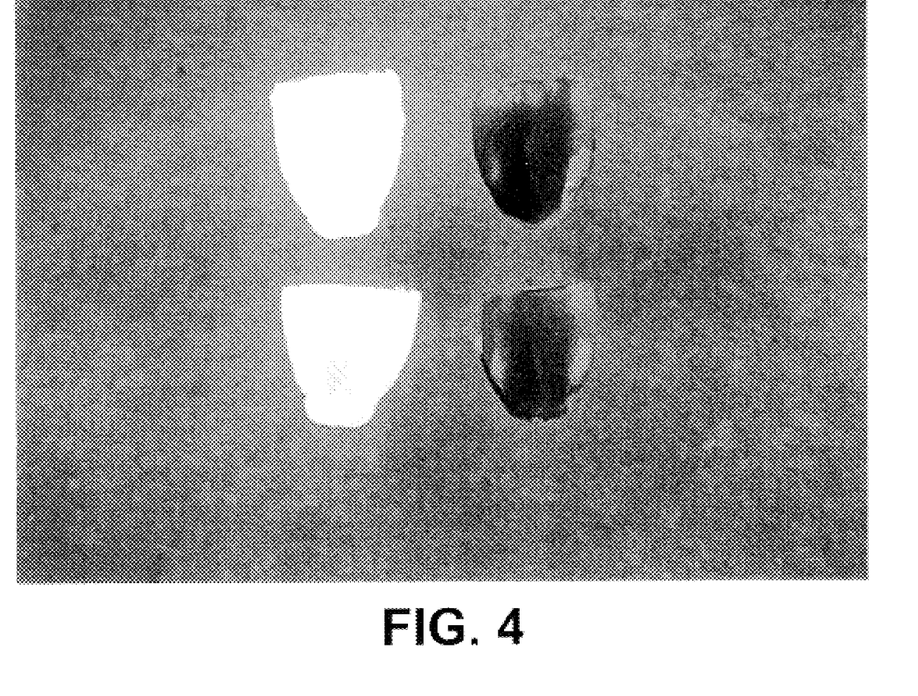

Results. The results are shown in FIG. 4 and Table 2. FIG. 4 shows GUS expression in immature seeds from a green fruit about 20 mm in diameter. The stained seeds were transformed with the GUS reporter gene and show GUS expression. The white seeds are control seeds. Table 2 also shows that GUS expression was obtained.

In sum, the results of our studies demonstrate the Agrobacterium-mediated transformation of floral buds.

TABLE 2

GUS Histochemical Assay for Immature Seeds

| Number of inoculation | Number of floral buds | Number of immature seeds | GUS Expression |
|---|---|---|---|
| 2 | 20 | 310 | Not found |
| 3 | 4 | 84 | 3 chimeric seeds |
| 4 | 7 | 129 | 3 homogeneously stained seeds* |
| 5 | 12 | 248 | 10 chimeric seeds |

*2 of these seeds are shown in FIG. 4.

Example 4

The following example describes transformation of castor using biolistic transformation of embryo axes and shoot tips.

Seeds were obtained from castor Accession, PI 215769 described in Example 1. The plasmid used is as described in Example 1. Culture Conditions are as described in Example 2.

Transformation. Plasmid pBISN1 is coated on gold particles. These particles are accelerated into embryo axis tissue and shoot tips by particle bombardment.

It is understood that the foregoing detailed description is given merely by way of illustration and that modification and variations may be made within, without departing from the spirit and scope of the invention. All publications and patents cited herein are hereby incorporated by reference in their entirety.

What is claimed is:

1. A method for transforming a castor plant, wherein the method comprises:
    (a) stably introducing by Aarobacterium-mediated transformation a transgene into a female flower bud of an intact castor plant to produce a transformed flower bud, wherein said Agrobacterium-mediated transformation comprises wounding of the flower bud and infiltration of Agrobacterium comprising the transgene,
    (b) allowing said transformed flower bud to develop and set seed,
    (c) collecting seed that comprises the transgene, and
    (d) growing the seed into a plant, wherein the plant comprises the transgene.

\* \* \* \* \*